(12) United States Patent
Besselink

(10) Patent No.: US 9,241,782 B2
(45) Date of Patent: Jan. 26, 2016

(54) BISTABLE SPRING CONSTRUCTION FOR A STENT AND OTHER MEDICAL APPARATUS

(75) Inventor: Petrus Antonius Besselink, Enschede (NL)

(73) Assignee: CELONOVA STENT, INC., San Antonio, TX (US)

( * ) Notice: Subject to any disclaimer, the term of this patent is extended or adjusted under 35 U.S.C. 154(b) by 139 days.

(21) Appl. No.: 12/941,591

(22) Filed: Nov. 8, 2010

(65) Prior Publication Data
US 2011/0208291 A1    Aug. 25, 2011

Related U.S. Application Data

(63) Continuation of application No. 10/270,771, filed on Oct. 11, 2002, now Pat. No. 7,828,836, which is a continuation of application No. 09/012,843, filed on Jan. 23, 1998, now Pat. No. 6,488,702.

(60) Provisional application No. 60/036,359, filed on Jan. 24, 1997.

(51) Int. Cl.
A61F 2/02       (2006.01)
A61F 2/04       (2013.01)
(Continued)

(52) U.S. Cl.
CPC .................. *A61F 2/042* (2013.01); *A61B 17/11* (2013.01); *A61F 2/0009* (2013.01); *A61F 2/0022* (2013.01); *A61F 2/02* (2013.01); *A61F 2/064* (2013.01); *A61F 2/91* (2013.01); *A61F 2/915* (2013.01); *F16K 31/003* (2013.01); *A61B 2017/1107* (2013.01); *A61F 2002/047* (2013.01); *A61F 2002/9155* (2013.01); *A61F 2002/91541* (2013.01); *A61F 2002/91558* (2013.01);

(Continued)

(58) Field of Classification Search
CPC ..... A61F 2/82; A61F 2/91; A61F 2250/0048; A61F 2250/0036; A61F 2250/0029
USPC ............. 623/1.1, 1.12, 1.15, 1.16, 1.17, 1.18, 623/1.19, 1.2, 1.3, 23.64, 23.7
See application file for complete search history.

(56) References Cited

U.S. PATENT DOCUMENTS 3,069,125 A    12/1962  Hewitt, Jr.
3,508,587 A     4/1970  Mauch
(Continued)

FOREIGN PATENT DOCUMENTS

DE    8812719     11/1989
EP    0274846 A1   7/1988
(Continued)

OTHER PUBLICATIONS

Australian Patent Application No. 2014201636 Examination Report dated Aug. 20, 2014.
(Continued)

*Primary Examiner* — David Isabella
*Assistant Examiner* — Suba Ganesan
(74) *Attorney, Agent, or Firm* — Mannava & Kang, P.C.

(57) ABSTRACT

The present invention is directed to bistable cells and their use in devices, particularly medical devices such as stents, clamps and valves. An expandable stent formed of a plurality of bistable cells is described. The stent has two or more stable configurations, including a first stable configuration with a first diameter and a second stable configuration with a second, larger diameter. A valve comprising a bistable cell for use in eliminating incontinence is also disclosed.

20 Claims, 14 Drawing Sheets

(51) Int. Cl.
*A61B 17/11* (2006.01)
*A61F 2/00* (2006.01)
*A61F 2/06* (2013.01)
*A61F 2/91* (2013.01)
*A61F 2/915* (2013.01)
*F16K 31/00* (2006.01)

(52) U.S. Cl.
CPC ............... *A61F2002/91575* (2013.01); *A61F 2230/0054* (2013.01); *A61F 2250/0039* (2013.01)

(56) References Cited

U.S. PATENT DOCUMENTS

| | | | |
|---|---|---|---|
| 3,657,744 | A | 4/1972 | Ersek |
| 3,898,717 | A | 8/1975 | Schwartz |
| 4,641,654 | A | 2/1987 | Samson et al. |
| 4,665,906 | A | 5/1987 | Jervis |
| 4,733,665 | A | 3/1988 | Palmaz |
| 4,739,762 | A | 4/1988 | Palmaz |
| 4,886,062 | A | 12/1989 | Wiktor |
| 4,969,890 | A | 11/1990 | Sugita et al. |
| 4,994,071 | A | 2/1991 | MacGregor |
| 5,102,417 | A | 4/1992 | Palmaz |
| 5,104,404 | A | 4/1992 | Wolff |
| 5,141,360 | A | 8/1992 | Zeman |
| 5,147,370 | A | 9/1992 | McNamara |
| 5,192,307 | A | 3/1993 | Wall |
| 5,197,978 | A | 3/1993 | Hess |
| 5,226,913 | A | 7/1993 | Pinchuk |
| 5,234,448 | A | 8/1993 | Wholey et al. |
| 5,354,308 | A | 10/1994 | Simon et al. |
| 5,383,892 | A | 1/1995 | Cardon et al. |
| 5,383,926 | A | 1/1995 | Lock et al. |
| 5,397,355 | A | 3/1995 | Marin et al. |
| 5,403,341 | A | 4/1995 | Solar |
| 5,411,507 | A | 5/1995 | Heckele |
| 5,449,373 | A | 9/1995 | Pinchasik et al. |
| 5,496,365 | A | 3/1996 | Sgro |
| 5,545,210 | A | 8/1996 | Hess et al. |
| 5,562,690 | A | 10/1996 | Green et al. |
| 5,601,593 | A | 2/1997 | Freitag |
| 5,643,314 | A | 7/1997 | Carpenter et al. |
| 5,695,516 | A | 12/1997 | Fischell et al. |
| 5,702,419 | A | 12/1997 | Berry et al. |
| 5,725,570 | A | 3/1998 | Heath |
| 5,733,303 | A * | 3/1998 | Israel et al. .................. 623/1.15 |
| 5,755,774 | A | 5/1998 | Pinchuk |
| 5,755,776 | A | 5/1998 | Al-Saadon |
| 5,776,181 | A * | 7/1998 | Lee et al. ..................... 623/1.15 |
| 5,776,183 | A | 7/1998 | Kanesaka et al. |
| 5,895,406 | A | 4/1999 | Gray et al. |
| 5,899,882 | A | 5/1999 | Waksman et al. |
| 5,922,020 | A * | 7/1999 | Klein et al. .................. 623/1.15 |
| 5,928,280 | A | 7/1999 | Hansen et al. |
| 6,013,854 | A * | 1/2000 | Moriuchi ..................... 623/1.11 |
| 6,019,789 | A | 2/2000 | Dinh et al. |
| 6,027,526 | A | 2/2000 | Limon et al. |
| 6,027,527 | A | 2/2000 | Asano et al. |
| 6,106,548 | A | 8/2000 | Roubin et al. |
| 6,206,911 | B1 | 3/2001 | Milo |
| 6,261,319 | B1 | 7/2001 | Kveen et al. |
| 6,264,685 | B1 | 7/2001 | Ahari |
| 6,368,355 | B1 | 4/2002 | Uflacker |
| 6,451,052 | B1 | 9/2002 | Burmeister et al. |
| 7,407,508 | B2 | 8/2008 | Kitaoka et al. |
| 2001/0027339 | A1 | 10/2001 | Boatman et al. |
| 2004/0034409 | A1 | 2/2004 | Heublein et al. |
| 2004/0193177 | A1 | 9/2004 | Houghton et al. |
| 2004/0193247 | A1 | 9/2004 | Besselink et al. |
| 2006/0217795 | A1 | 9/2006 | Besselink et al. |
| 2006/0241739 | A1 | 10/2006 | Besselink et al. |
| 2008/0097571 | A1 | 4/2008 | Denison et al. |

FOREIGN PATENT DOCUMENTS

| | | |
|---|---|---|
| EP | 0326426 | 8/1989 |
| EP | 0335341 A1 | 10/1989 |
| EP | 0364787 | 4/1990 |
| EP | 0421729 | 4/1991 |
| EP | 0540290 A2 | 5/1993 |
| EP | 0587197 | 3/1994 |
| EP | 0636345 | 2/1995 |
| EP | 0664107 | 7/1995 |
| EP | 0679372 | 11/1995 |
| EP | 0688545 | 12/1995 |
| EP | 0734698 | 10/1996 |
| EP | 0744164 | 11/1996 |
| EP | 0824902 | 2/1998 |
| EP | 1223305 | 7/2002 |
| FR | 2617721 A1 | 1/1989 |
| FR | 2642812 | 8/1990 |
| GB | 2081173 | 2/1982 |
| GB | 2169515 | 7/1986 |
| GB | 2175824 A | 12/1986 |
| JP | S62-072372 | 4/1987 |
| JP | H01-299550 | 12/1989 |
| JP | H04-505569 | 10/1992 |
| JP | H09-099095 | 4/1997 |
| JP | H10-080493 | 3/1998 |
| JP | 2001-511030 | 8/2001 |
| JP | 2002-045432 | 2/2002 |
| JP | 2002-522174 | 7/2002 |
| JP | 2002-272855 | 9/2002 |
| JP | 2002332791 | 11/2002 |
| JP | 2003-515383 | 5/2003 |
| JP | 2004-097804 | 4/2004 |
| JP | 2004-121342 A | 4/2004 |
| JP | 2004-298640 | 10/2004 |
| JP | 2005-279076 | 10/2005 |
| WO | WO 92/06734 A1 | 4/1992 |
| WO | WO 92/19310 A1 | 11/1992 |
| WO | WO 93/22986 | 11/1993 |
| WO | WO 94/03127 A1 | 2/1994 |
| WO | WO 95/09584 | 4/1995 |
| WO | WO 95/31945 | 11/1995 |
| WO | WO 95/32757 | 12/1995 |
| WO | WO 96/03942 | 2/1996 |
| WO | WO 96/09013 | 3/1996 |
| WO | WO 96/18359 | 6/1996 |
| WO | WO 96/29028 | 9/1996 |
| WO | WO 96/41589 | 12/1996 |
| WO | WO 97/04721 | 2/1997 |
| WO | 01/26584 | 4/2001 |
| WO | WO 01/26584 A1 | 4/2001 |

OTHER PUBLICATIONS

International Search Report, dated Sep. 16, 1998, re PCT/US98/01310 in 12 pages.
European Search Report, dated Mar. 15, 2006, re EP 05 02 2622 in 4 pages.
European Examination Report, dated Jul. 21, 2008, re EP 05 02 2622 in 4 pages.
Japanese Patent Application No. JP 2014-151979 Examination Report dated Jun. 25, 2015, Japanese Patent Office, With English Translation, 16 pages.

* cited by examiner

BISTABLE SPRING CONSTRUCTION FOR A STENT AND OTHER MEDICAL APPARATUS

CROSS-REFERENCE TO RELATED APPLICATIONS

This application is a continuation of U.S. application Ser. No. 10/270,771, filed on Oct. 11, 2002, to be issued as U.S. Pat. No. 7,828,836, which is a continuation application of U.S. application Ser. No. 09/012,843, filed Jan. 23, 1998, now U.S. Pat. No. 6,488,702, which claims priority to U.S. Provisional Application No. 60/036,359, filed on Jan. 24, 1997, all of which are each hereby incorporated by reference as if set forth herein in their entireties.

BACKGROUND OF THE INVENTION

There are several kinds of stents on the market with either balloon expandable or self expanding function. Balloon expandable stents are generally made from a material that can easily be plastically deformed into two directions. Before insertion, the stent is placed around the balloon section at the distal end of a catheter and pressed together to reduce the outer dimensions.

As soon as the stent is brought into the body in the proper axial position it can be expanded and thereby plastically deformed by pumping up the balloon. In this final position, the stent is at its largest diameter and should function to support the surrounding tissue, preventing an undesired shape change into a much smaller diameter, at least locally.

Therefore, the stent needs to have sufficient rigidity in the radial direction, but also some flexibility in the axial direction when it is in the final position. Further, the amount of material should be as small as possible and in the inner surface of the stent should not obstruct the flow through the channel (e.g., for blood) or cause too much turbulence.

Problems that generally occur with these stents are as follows: After compressing the stent to its smallest diameter around the balloon, the stent will always have some elastic spring back to a slightly larger diameter, which can cause problems when the catheter is brought into the patient's body. In addition, the axial friction between balloon and stent can become so small that the stent slips off the catheter. Further, a larger size stent is typically a disadvantage.

A further problem is the so called recoil of these stents. This means that after expansion by the balloon pressure, the outer diameter will always become slightly smaller as soon as the balloon is deflated. This degree of recoiled can be as much as 10%, which can cause migration of the stent.

A different type of stent is made of a more or less elastically expanding structure, which has to be held on the catheter by some external means. An example of this type is a stent that is held in its constrained state by a delivery sheath, that is removed at the moment that the stent should deploy to its natural form.

Some of these stents are made of shape memory material with either superelastic behavior or temperature sensitive triggering of the expansion function.

A disadvantage of these self-expanding stents is the need for the delivery sheath, causing a larger insertion diameter. The removal of the sheath also requires a sheath retraction mechanism, which has to be activated at the proximal end.

Most stents of both types further have the disadvantage of relatively large length change during expansion and a poor hydrodynamic behavior because of the shape of the metal wires or struts.

Another disadvantage of some stents is the positive spring rate, which means that further expansion can only be achieved by higher balloon pressure.

The construction of prior stents is typically made in such a way that the external forces, working on the stent in the radial direction, merely cause bending forces on the struts or wires of the structure.

For example, a unit cell of a Palmaz-Schatz-stent, as produced by Johnson & Johnson Interventional Systems or the ACT One Coronary stent, produced by Progressive Angioplasty Systems, Inc. has in its collapsed condition a flat, rectangular shape and in its expanded condition a more or less diamond-shaped form with almost straight struts (Palmaz-Schatz) or more curved struts (ACT-One).

The shape of the unit cell of such stents is typically symmetrical with four struts each having the same cross section. In addition, the loading of the cell in the axial direction will typically cause an elastic or plastic deformation of all of the struts, resulting in an elongation of the unit cell in the axial direction. These unit cells have a positive spring rate. In stents based upon these unit cells the stability against radial pressure is merely dependent on the banding strength of the struts and their connections.

BACKGROUND OF THE INVENTION

In this patent application a new type of stent is described with a unit cell, having a negative spring rate and a bistable function. Such a unit cell can also be used in other medical applications. This means that it has two configurations in which it is stable without the need for an external force to hold it in that shape. The unit cell is formed using at least two different sections. One section is less pliable than the other one and acts a relatively rigid support that hinders the shape change of the more pliable section in one direction. In the other direction the pliable section can be deformed, but because of the opposing force from the rigid section, the stability of the pliable or flexible section is strongly increased.

External forces in a direction perpendicular to the most pliable section are distributed to the rigid section and the cross section of the pliable section is merely loaded in compression mode. This makes the construction much stronger than prior stents. In prior stents, all struts have generally the same cross section and mechanical properties and are merely used in the bending mode.

The construction of a stent, based upon this unit cell results in an apparatus, that can easily be elastically compressed around the balloon by finger pressure.

Below a certain critical diameter, the present stent snaps further to a stable, smallest diameter, thus holding the deflated balloon firmly on to the surface of the catheter, with an insertion diameter that is as small as possible. An additional sheath is not required, but may be used for extra safety.

After the stent has been brought into the patient's body at the proper axial position, the balloon can be inflated until the stent reaches its critical elastic equilibrium diameter. Slightly above this diameter the stent automatically expands further to its final largest diameter, where it reaches its maximum stability against radial pressure. The design enables a constant length large expansion ratio, a reliable expandability and/or a small surface ratio.

A further embodiment of this invention is the possibility of a kind of stepwise expanding stent with a range of stable diameters.

Another part of the invention is a stent with several external diameters along its length, to adapt as good as possible to the shape of the body cavity where it is placed.

Another part of the invention is the possibility to modify the stress and strain pattern in the unit cell by means of a heat treatment in such a way, that the force displacement characteristic of this unit cell becomes asymmetrical or even exhibits a monostable instead of a bistable function, either with the expanded diameter or the collapsed diameter being the most stable condition.

Another embodiment of the invention is the modification of the geometry of the cross section of some struts to achieve the symmetric or asymmetric bistable or monostable force against displacement characteristics of a unit cell.

Another part of the invention is the use of one or more unit cells in other medical applications such as, for example, an expander or a clip, either to spread a body cavity open or to clamp or hold a body part or some body tissue.

The invention is also directed to the use of the inventive stents in conjunction with inventive expander rings to join together two vessels.

The invention is also directed to a bistable valve having a snap-action bipositional unit cell and uses for the same, in particular, to prevent incontinence.

The invention is also directed to multistable cells and their use in medical devices.

DESCRIPTION OF THE CONSTRUCTION

The construction of the present stent includes a series of elements with an arrangement of unit cells that enable the stability in a special way. Each unit cell exists out of at least two distinct, mechanically connected sections with different mechanical behaviors. One section acts as a relatively rigid support for the more flexible counteracting section. The more flexible section is responsible for most, if not all, of the expansion of the stent. There are several ways to manufacture a stent based upon this principle and it can be made from several materials, like polymers, composites, conventional metals or shape memory alloys with superelastic behavior or with temperature sensitive behavior.

It can be made from an arrangement of wire or strip, welded together at specific places. Another possibility is metal deposition in the desired pattern onto a substrate or the use of sintering of prealloyed powder.

A further method is making the stent from a tubular shaped starting material, with a pattern of slits or slots made in the wall by means of etching, grinding, cutting (e.g., with a laser, water, etc.), spark erosion or any other suitable method. The pattern can also be made in a flat plate and then welded, brazed or crimped to a more or less cylindrical shape or a cylindrical mid section with two conical ends with larger diameters.

BRIEF DESCRIPTION OF THE DRAWINGS

Figure 1A:
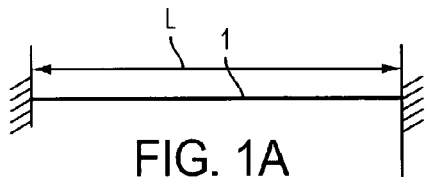
FIG. 1 shows the principle of a bistable mechanism.
Figure 1B:
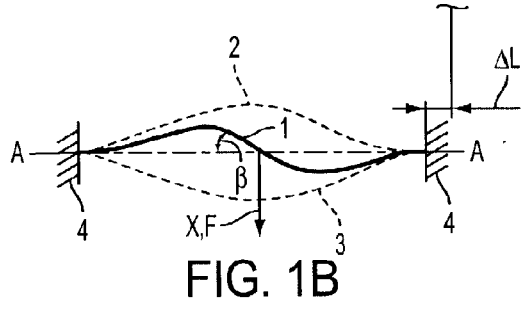
Figure 1C:
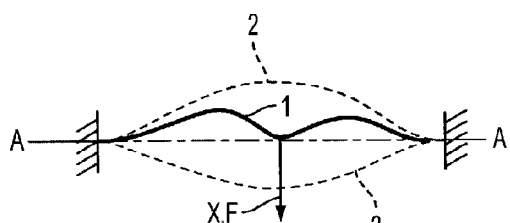

FIG. 1 shows the principle on which the stent is based, FIG. 1a shows a rod 1 with a length L, which is compressed in its axial direction unit; it reaches its buckling stress. Then the central part of the rod will band out in a sidewards direction, either to position 2 or 3 (dashed lines in FIG. 1b). When the axial displacement L of the ends of the rod is held stable by external clamps 4, it is possible to move the central section of the rod between the two stable positions 2 and 3. This movement is in a direction X, perpendicular to the original length axis A-A of the rod. All positions between the stable positions 2 and 3 are unstable. In FIG. 1b the central part of the rod has to rotate over an angle β before the rod can be moved in direction X. FIG. 1C shows a second order curvature in rod 1, which occurs when the rotation over angle β is opposed by clamping the central part of rod 1 and maintaining this part parallel to the axis A-A.

Figure 2:
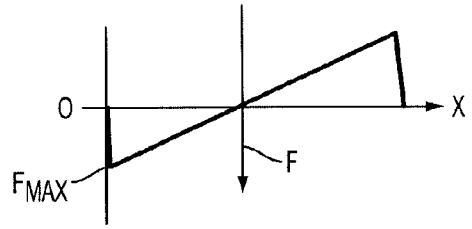
FIG. 2 shows the force-displacement characteristic of the mechanism of FIG. 1.

FIG. 2 shows the force F as a function of displacement X, with X displayed in the horizontal direction. The rod is moved from the upper 2 to the lower 3 stable position of FIG. 1. The force increases rapidly from zero to Fmax. At that moment the onset of either the first or second order curvature of FIGS. 1b and 1c is reached. Further displacement in direction X costs less force, because this spring system has a negative spring rate. The force even becomes zero in the mid position and further movement occurs automatically. It can be seen in FIG. 2 that the system is completely symmetrical and the force needed to move back from the lower to the upper position has the same characteristic.

Figure 3:
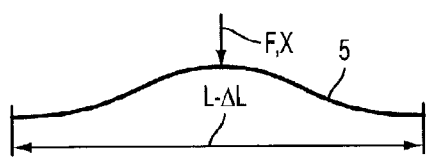
FIG. 3 shows another bistable mechanism with an asymmetric bistability.

FIG. 3 shows rod 5, which will have an asymmetrical force displacement characteristic, because it already has a preset curvature, even in the unloaded position, where the length is already L-L. This can be achieved by prior plastic deformation, heat treatment or the use of an asymmetrical geometry of the cross section of the rod (not shown). The rod 5 in FIG. 3 can be mounted between two clamps on a length L-L, and if it is elastically deformed in the same way as the rod in FIGS. 1b and 1c, it will have a different stress distribution in the cross section in end position 2 and 3, compared to the rod of FIG. 1. This means that the rod has become a preferent unloaded table position, shown in FIG. 3.

Figure 4:
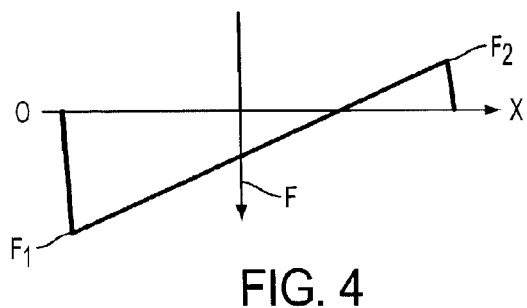
FIG. 4 shows the force-displacement characteristic of the mechanism of FIG. 3.

FIG. 4 shows the asymmetrical force-displacement characteristic of the precurved rod of FIG. 3. The initial displacement form the stable upper position needs a starting force F1 and if the rod is in its table lower position the starting force in the opposite direction is only F2, being smaller than F1. Force F2 can be made as small as desired, even zero or negative, but needs to have a positive value if stability of the lower position is required.

Figure 5A:
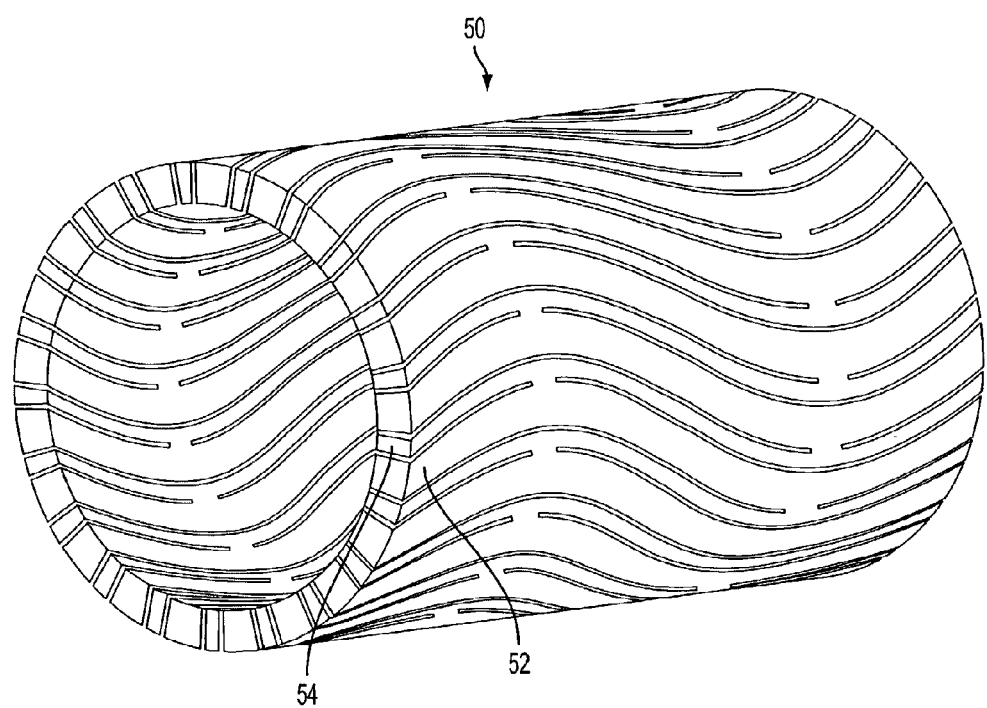
FIG. 5a shows an inventive tubular stent in the stable, fully collapsed configuration.
Figure 5B:
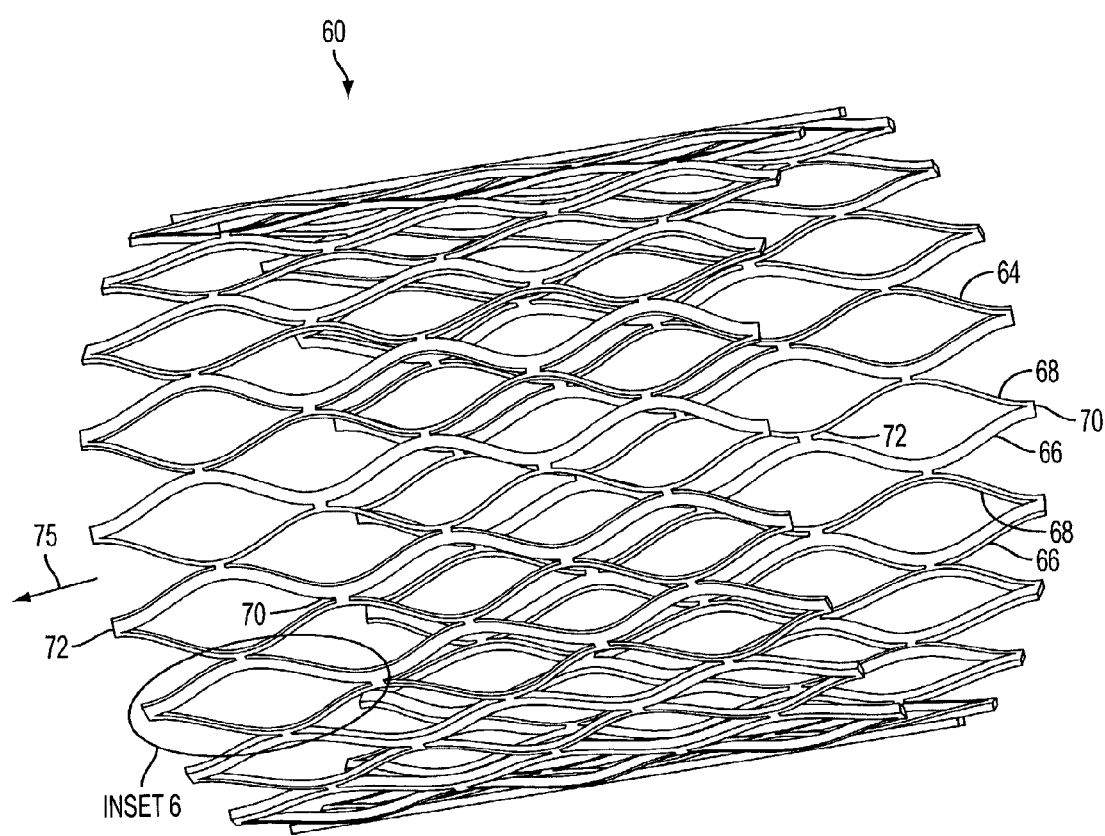
FIG. 5b shows an inventive tubular stent in the stable fully expanded configuration.

FIGS. 5a and 5b show the general appearance of an inventive tubular stent in fully contracted and fully expanded configuration respectively. The stent, in its fully contracted state shown generally at 50 and in its fully expanded state shown generally at 60, is comprised of a plurality of interconnected bistable unit cells (shown in the expanded state at 64 in FIG. 5b). The bistable unit cells are formed from a first relatively rigid segment 52 (66 in FIG. 5b) and a second relatively flexible segment 54 (68 in FIG. 5b), joined together at ends 70 and 72. Second relatively flexible segments 68 are interconnected with adjacent relatively rigid members 66. Adjacent cells in the longitudinal sense (the longitudinal axis is denoted by reference numeral 75) are joined at ends 70 and 72. By applying a uniform radially outward or inward force, the stent may be switched directly from a fully contracted to a fully expanded configuration or vice versa.

Figure 6:
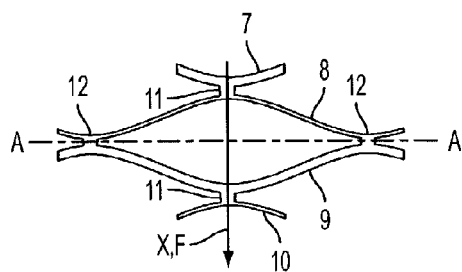
FIG. 6 shows a part of a stent with one bistable unit cell, drawn in the stable expanded shape.

FIG. 6 (corresponding to inset 6 in FIG. 5b) shows a small part of a stent such as that shown in FIG. 5 which uses the bistable function of a unit cell, according to the present invention. The drawing shows a horizontal line A-A, which is parallel to the central axis of the stent. There are two series of sinusoidal segments with distinct size (see also FIG. 9 for an overview). The segments 7 and 9 have a relatively large cross section. Only segment 9 is shown entirely. The segments 9 and 10 have a relatively smaller cross section, and here only segment 8 is entirely shown. The segments are interconnected for example welded, at joints 11 and 12.

Because of the difference between the cross section of segment 8 and 9, the deformation force of segment 8 is much lower than for segment 9. Therefore, segment 9 can be considered as a relatively rigid clamp, like the clamps 4 in FIG. 1b opposing relative displacement between the joints 12 in the axial direction, parallel to axis A-A. In contrast, segment 8 acts as a flexible rod, like rod 1, described in FIG. 1 or rod 5, described in FIG. 3. This combination of segments 7 and 8 or 9 and 10 defines a unit cell, acting as a bistable spring system with a force-displacement curve F-X like the described curves of FIGS. 2 and 4, depending on the unloaded condition and geometry of the segments. Alternatively, instead of using segments or struts of different diameter, the segments can have the same diameters (i.e., cross sectional area) and exhibit different strengths or rigidity and still accomplish the same effect. One way to obtain such differences in strength or rigidity would be to use different materials for the segments. Another way would be to use the same material, like a metal, for all the segments but selectively strengthen (e.g., by heat treating) those segments that need to be rigid. It should be noted that heat treatment will not strengthen all materials. Nitinol, for example becomes more pliable as a result of heat treatment. This property of Nitinol can be exploited, however, to render one section of Nitinol more pliable relative to a second, non-heat-treated section of Nitinol.

Figure 7:
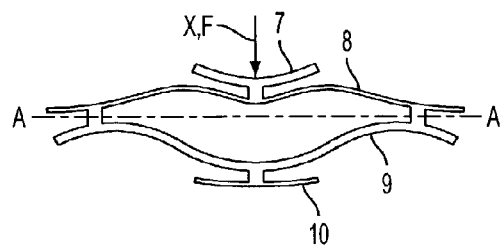
FIG. 7 shows the part of the stent of FIG. 6 near its elastic bistable equilibrium position.

FIG. 7 shows the same part of the stent (as depicted in FIG. 6) near the elastic equilibrium position. Segment 8 has been deformed into the direction X, caused by force F, but segment 9 has almost its original shape, because of its larger rigidity.

Figure 8:
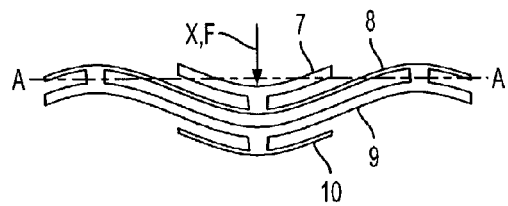
FIG. 8 shows the part of the stent of FIGS. 6 and 7 in its stable collapsed shape.

FIG. 8 shows the same unit cell of the stent of FIGS. 6-7 after it has been pressed through the elastic equilibrium position. It automatically snaps into its stable position of FIG. 8. This snapping force can be strong enough to hold a deflated balloon tight on the catheter shaft (not shown), depending on the mechanical characteristics (e.g., the strength) of the material(s) used to make the segments. With the geometry shown in these figures, the segments 8 and 9 fit close together, taking up a minimum amount of space when the stent is in its smallest stable diameter.

Figure 9:
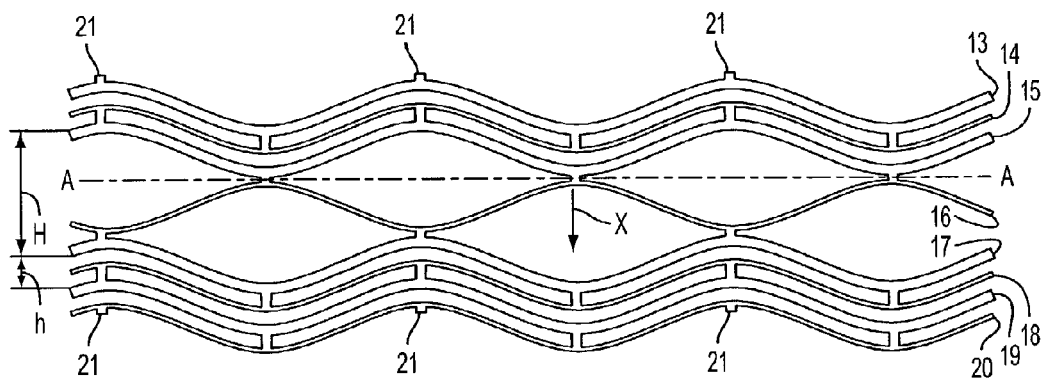
FIG. 9 shows a larger section of the stent of FIGS. 6 and 8, showing some unit cells in the collapsed shape and some unit cells in the expanded shape.

FIG. 9 shows a section of the stent of FIG. 5, flattened for illustrative purposes, showing several flexible segments in the collapsed stable shape (segments 14, 18 and 20) and one segment element 16 in the expanded stable shape. Segments 13, 15, 17, and 19 are relatively rigid segments and substantially maintain their original shape. The distance between two relatively rigid segments is shown as (h) in the collapsed stable shape and (H) in the expanded stable shape. The value of the displacement (H-h) in the direction X depends on the height of an expanded unit cell or amplitude of the segments and the size of the connecting joints. The described part of the stent is shown as a flat surface, but it may be clear that a cylindrical stent such as that shown in FIG. 5 is shaped if segments 13 and 20 are directly connected to reach other with joints 21. In other words, the stent is shown separated along the joints 21 and in a flattened condition.

The range of stable diameters of the stent changes with the value $(H-h)/\pi$, each time that a flexible segment snaps from the collapsed stable position to the expanded stable position. The result is a stent with an extremely rigid surface at all diameters being able to withstand the external forces better than with conventional stents. In the length direction, the flexibility of the stent can be increased by disconnecting several unit cells from their neighbor unit cells, for example, by cutting the center of one or more joints while maintaining the several joint pieces as joints.

Another method to increase flexibility is to change the geometry of several sections of the unit cells in the length direction from the relative flexible to the relative rigid shape several times along the total length of the stent. In other words, referring to FIG. 9 one or more or each of the segments 13-20 could be constructed with larger and smaller diameter (or otherwise flexible and rigid) sections which alternate after each joint 21.

Figure 10:
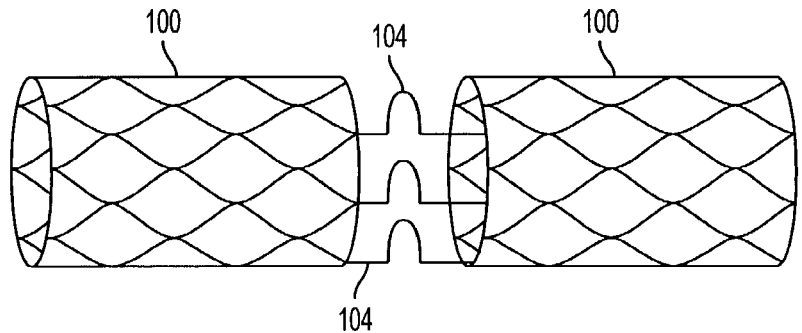
FIG. 10 shows an inventive stent formed of a plurality of smaller inventive stents joined together with flexible connectors.

Another possibility, as shown in FIG. 10 is the use of a series of short multistable stents 100 aligned lengthwise end to end and connected with flexibility joints 104 having the same or a different geometry or configuration as the joints forming individual unit cells.

The scope of the invention should include all types of material. One of the most interesting materials is superelastic Nitinol, because of its large elastic strain, well defined stress values, caused by their plateau stresses and the possibility to define the desired curvature into the metal by means of a heat treatment. A stent of Nitinol can be made by forming slits or slots in a tube, while in its collapsed or smaller stable diameter. The slotted tube is then expanded by a separate shaping tool and heat treated on this tool to define the expanded stable diameter as the unstrained shape.

In a more general sense, the present invention is directed to a device having a plurality of stable configurations. The device is comprised of a plurality of interconnected multistable cells. The cells include one or more relatively rigid sections and one or more relatively flexible sections interconnected so as to define a cell structure in the form of a multistable spring system having a plurality of stable configurations. In a preferred embodiment, the cells comprise a first arcuate member having first and second ends and a second arcuate member having first and second ends, the first end of the first member in communication with the first end of the second member, and the second end of the first member in communication with the second end of the second member. It should be noted, however that members need not be rigorously arcuate. Other shaped members, including relatively straight members are contemplated as well.

Figure 11:
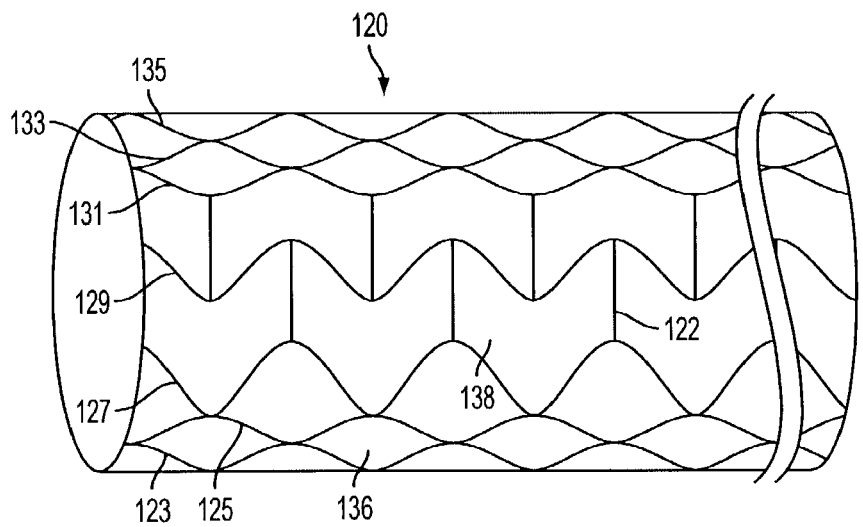
FIG. 11 shows a partially expanded inventive stent having more than one type of bistable unit cell.

The invention, in particular, contemplates bistable cells, that is cells having two stable configurations. In one such cell, the distance between corresponding points on the first and second sections is larger in the first stable state of the cell than in the second stable state of the cell. The cells themselves are constructed and arranged so that the device itself is at least bistable and possibly multistable. One such device, a cylindrical stent having two or more configurations with an initial diameter size and a final larger diameter size has been described above. However, mutistable stents are also contemplated. Thus, for example, a stent may be constructed in which the cells are designed and arranged to provide a range of diameters in step-wise fashion. One such way this may be accomplished would be to employ several different types of cells in the stent, each type of cell having a different spring constant so that depending on the amount of force used, the stent would assume a different diameter. Such a stent in a partially expanded state is shown schematically in FIG. 11. A partially expanded stent is shown generally at 120. The stent is comprised of relatively rigid segments 123, 127, 131 and 135 which substantially maintain their original shape, and relatively flexible segments 125, 129, and 133. The segments are interconnected, with joints 122. As depicted, first flexible elements 125, and 133 are in an expanded configuration while second flexible element 129 is in a contracted configuration. By applying a radially outward or tangential force, flexible element 129 may be flipped to its fully expanded configuration resulting in a stent (not shown) with a larger diameter. As shown in FIG. 11, cells 138 are larger than cells 136 even in the contracted state. First flexible elements 125 and 133 are characterized by a different degree of flexibility than second flexible element 129.

Figure 12:
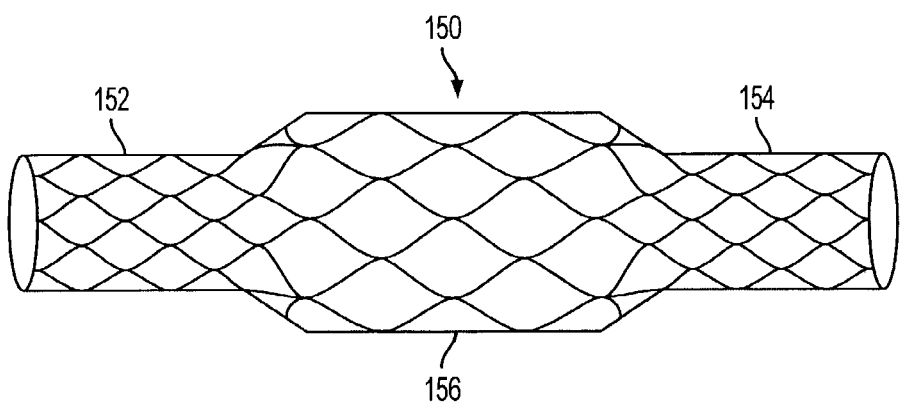
FIG. 12 shows an inventive stent having a range of diameters along its length.

Another form of stent, as shown generally at 150 in schematic FIG. 12, has an first diameter at a first end 152, a second diameter at a second end 154 and one (or more) intermediate diameters in a region 156 between first end 152 and second end 154, the intermediate diameter differing from the first and second diameters. The interconnected cells in such a stent, as shown generally at 150 in FIG. 12 may all have the same force constant and hence be openable all at once with the application of the necessary force or there may be several different types of cells, each with their own force constant. In order to achieve the multiplicity of diameters, cells of differing sizes may be used. In one embodiment of this type of stent, the first and second diameters are the same while in another embodiment, the first and second diameters differ.

The present invention is also directed to a method of implanting an expandable stent having a plurality of stable configurations. The method comprises the steps of applying the stent to an expanding means on a catheter, delivering the stent to a desired bodily location, expanding the expanding means so as to expand the stent from a first stable configuration to a desired second stable configuration, the second stable configuration having a larger diameter than the first stable configuration, and deploying the expanded stent at the desired bodily location. The expanding means may be a balloon, a mechanical device on or in the catheter, a heat source where the cells can be induced to change states by heating or any other suitable expanding means. The stent may be applied to the balloon in the first stable configuration or may be applied in the second stable (expanded) configuration during the applying step. In the latter case radially inward pressure may be applied to the stent so as to urge the stent into the first stable configuration to snap it onto the catheter. Where the stent has additional stable states, the stent may be applied to the balloon in an intermediate stable state in which the diameter of the stent is intermediate between the diameter in the first state and the diameter in the second state. Again, the stent may be locked on the expanding means by further applying a radially inward pressure.

Figure 13:
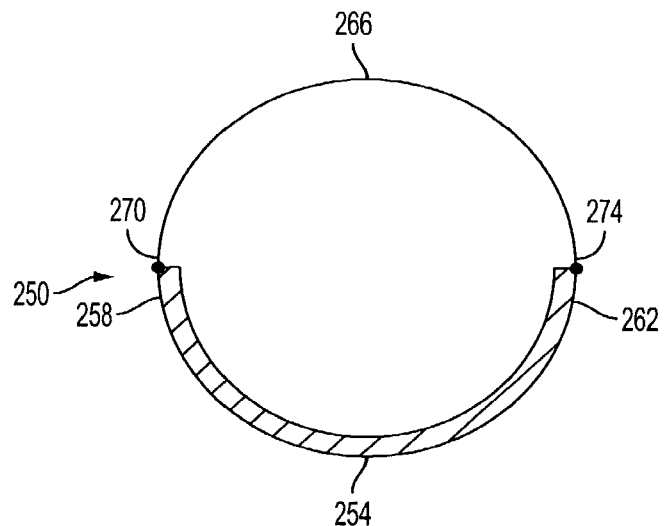
FIG. 13 shows an inventive expansion ring in expanded state.
Figure 14:
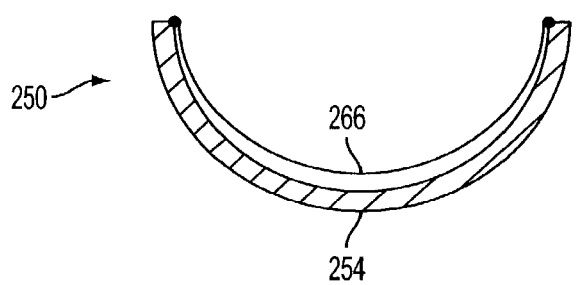
FIG. 14 shows the expansion ring of FIG. 13 in contracted state.

A further object of the invention is the use of a single bistable unit cell as an expander (expansion ring), that can be brought into a narrow place and then triggered to snap back into its expanded stable shape. As shown in FIG. 13 an expansion ring shown generally in its expanded state at 250 consists of a first rigid member 254 having first 258 and second 262 ends and a second more flexible member 266 having first 270 and second 274 ends. First end 258 of first member 254 is connected to first end 270 of second member 266 and second end 262 of first member 254 is connected to second end 274 of second member 266. FIG. 14 depicts the expansion ring of FIG. 13 in its contracted state. Second member 266 is seen to be in a second stable position.

Another object of the invention is the use of a single bistable loop (unit cell) as a clip, that can be used to clamp on an artery, fallopian tube or any other body part, to close or hold it for some time. For such a clip it may be desirable to define the collapsed stable shape as the unstrained shape, because the collapsed stable shape has to be the most stable one. In the collapsed state, the clip would resemble the collapsed expansion ring of FIG. 14. A triggering means would be used in conjunction with the clamp to switch the bistable loop from one state to another. The triggering means may be pneumatic, hydraulic, mechanical, thermal or electromechanical means. Examples of such triggering means include a human hand applying force to the bistable loop, and the application of heat to the loop. Other triggering means include pulling on the device, pushing on the device, bending the rigid section of the device or release a restraint holding the flexible member in place.

Another part of the present invention involves constructions between one or more ring-shaped elements according to the present invention, combined with a tubular sleeve that is reinforced or held open with such elements. An example is a so-called graft stent made of a polymer with one or more expansion rings. The expansion rings may consist of the above-described bi-stable cells. The surface of the stent comprises a skin mounted on the expansion rings. In mounting the skin, the skin may surround, be in or between the expansion rings. The skin may be human or animal skin, a polymeric material or any other suitable bio-compatible material. Such a stent may comprise one or more expansion rings, such as a first expansion ring at a first end of the stent and a second expansion ring at a second end of the stent. The stent may be of constant diameter along its length or may have a first diameter at the first end and a second diameter at the second end.

The present invention is also directed to a stent having an unexpanded configuration and an expanded configuration, and comprising a plurality of generally longitudinal, wave-like first members characterized by a first wavelength, and having peaks and troughs and a plurality of generally longitudinal wave-like second members characterized by a second wavelength, and having peaks and troughs. The wavelengths of the first and second longitudinal members are substantially equal. The second members are capable of stably assuming two positions, a first position corresponding to the unexpanded configuration in which the first and second members are in phase and a second position corresponding to the expanded configuration, in which the first and second members are 180.degree. out of phase. The first members are more rigid than the second members. The first and second longitudinal members are disposed on the surface of the stent such that the longitudinal first and second members alternate. In the unexpanded state, each peak of each first member is connected to one adjacent peak of a second member in a region of attachment and each trough of each first member is attached to one adjacent trough of a second member in a region of attachment, as can be seen from FIG. 8. The regions of attachment are separated along the longitudinal direction by one wavelength. The so described stent can be snapped from the unexpanded configuration to the expanded configuration by applying a radially outward force and similarly can be snapped from the expanded to the unexpanded configuration by applying a radially inward force. While such stents may be used internal to a bodily vessel, it may also be used external to vessels to join two vessels together.

Figure 15:
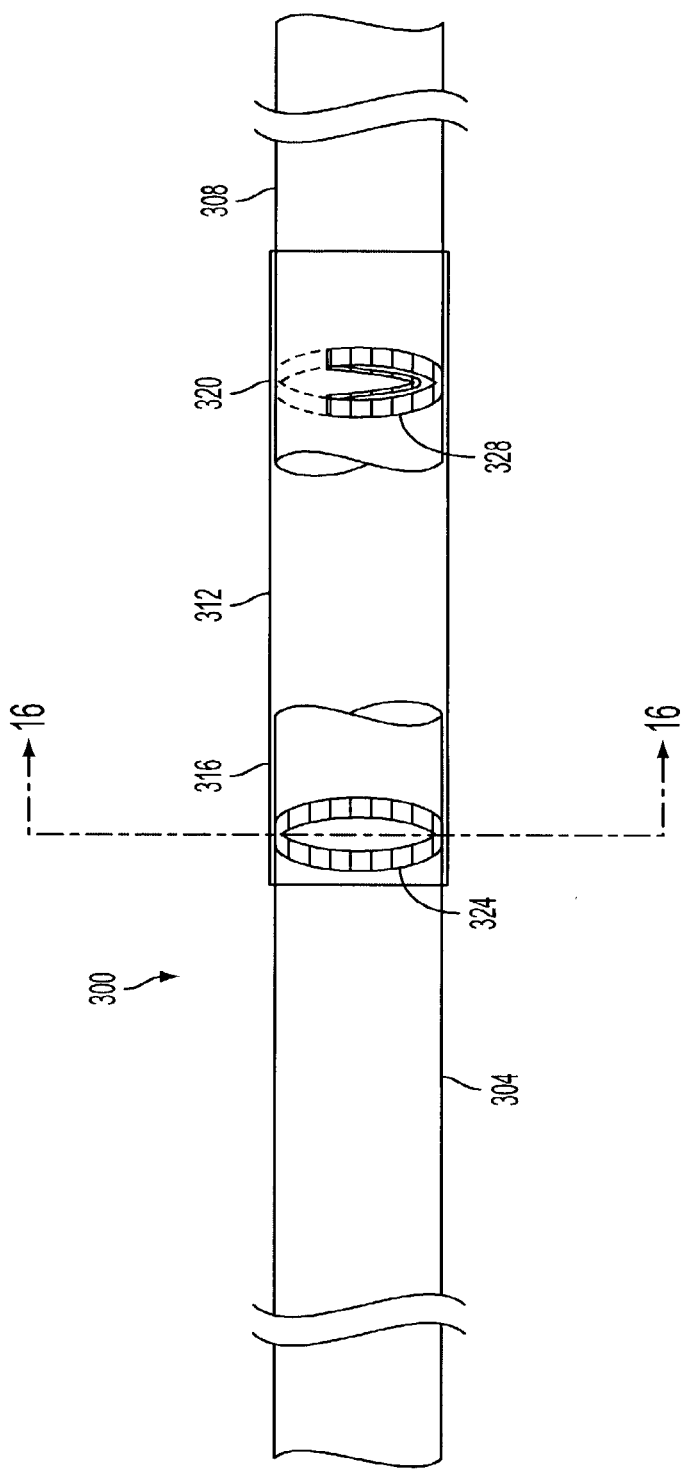
FIG. 15 shows an inventive stent joining two vessels together and further secured with inventive expansion rings, the stent exterior to the vessels.
Figure 16:
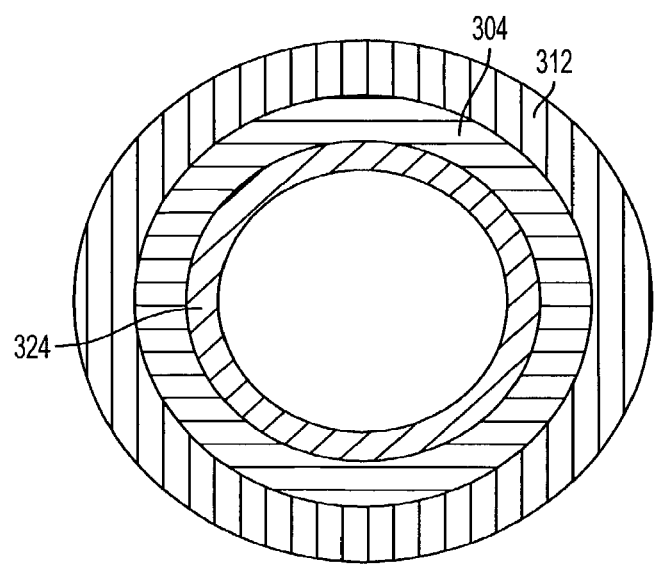
FIG. 16 shows a cross-sectional view of FIG. 15 along section line 16-16.

The invention also contemplates a method of joining together two vessels comprising the steps of delivering an inventive stent in an unexpanded configuration in a first stable state to a bodily site, expanding the stent to a second stable state, the diameter of the stent in the second stable state exceeding that of the vessels to be joined and placing the stent over the vessels to be joined. The stent may then be contracted to a third stable state, the stent in the third stable state having a diameter intermediate between the diameters of the stent in the unexpanded state and in the second stable state. The stent may further be secured to the vessel with the aid of one or more of the above-described expansion rings (a bistable loop). One or more expansion rings, such as that depicted in FIGS. 13 and 14 or small clamping stents (such as that formed from the strip shown in FIG. 23) may be delivered to each side of the stent in a contracted state and deployed so as to clamp the vessels between the ring(s). Multiple rings may be used for additional clamping. As shown generally at 300 in FIG. 15, a first vessel 304 and a second vessel 308 are joined together with inventive stent 312. Vessel 304 overlaps stent 312 in a first overlap region 316 while vessel 308 overlaps stent 312 in a second overlap region 320. Vessel 304 is clamped between expansion ring 324 (shown in the expanded state) and stent 312 while vessel 308 is clamped between expansion ring 328 (shown in the unexpanded state for illustrative purposes only) and stent 312. the dotted lines associated with expansion ring 328 illustrate expansion ring 328 in its expanded state. It should be additionally noted that FIG. 15 provides a cut-away view of vessels showing the rings contained therein. FIG. 16 shows a cross-sectional view of FIG. 15 along section line 16-16. Vessel 304 is shown sandwiched between stent 312 and expansion ring 324.

Figure 17:
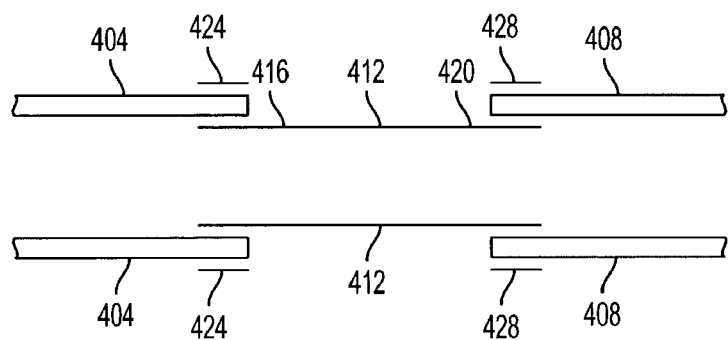
FIG. 17 shows an inventive stent joining two vessels together, the stent interior to the vessels.

In another embodiment, as shown in FIG. 17, a first vessel 404 and a second vessel 408 are joined together by a stent 412. First end 416 of stent 412 rests in vessel 404 while second end 420 of stent 412 rests within vessel 408. Optional clamps (such as a small portion of a collapsible inventive stent shown later in strip form in FIG. 23) 424 and 428 residing on the outside of vessels 404 and 408 clamp the stent to the vessel. Additional clamps may be used as needed.

In another embodiment, a combination of the embodiments of FIGS. 15 and 17, the first end of the stent may protrude from one of the vessels and the second end of the stent may extend over the second vessel. Again, clamps and expansion rings may be used to further secure the stent to the vessels.

Figure 18:
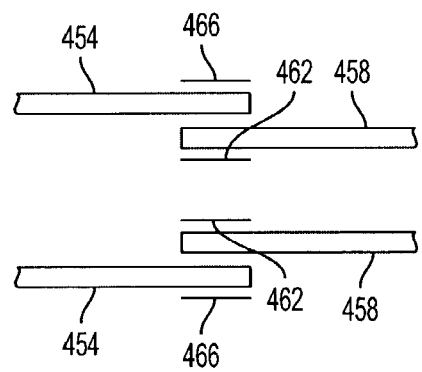
FIG. 18 shows two vessels joined together with an inventive expansion ring and a clamp

In another embodiment, as shown in FIG. 18, vessel 454 and vessel 458 are held together by an expansion ring 462 internal to the vessel and a clamp 466, consisting of, for example, a small section of collapsible stent, the stent chosen so that the diameter of the stent in a collapsed state affords a snug fit with vessels 454 and 458 and expansion ring 462. Either the expansion ring or the clamp, but not both, may be replaced by a suitable support such as a rigid collar.

The invention also contemplates a method of joining together two vessels comprising the steps of delivering an inventive stent in an unexpanded configuration in a first stable state to a bodily site, placing two bodily vessels over the stent and expanding the stent to a second stable state, the diameter of the stent in the second stable state exceeding that of the vessels to be joined. The diameter of the stent in the second stable state is preferably chosen so that the vessels fit snugly over the stent. The delivery of the stent may be accomplished by delivering the stent in an unexpanded configuration through a bodily vessel and subsequently expanding the stent to rest snugly in the vessels to be joined (where a portion of the stent resides in a vessel), or by expanding the stent to its most expanded state, placing the stent over the vessel and then contracting the stent to an intermediate state over the vessel. The collars and expansion rings mentioned above may similarly be delivered. Alternatively, the stent, collars and expansion rings may be delivered by surgically exposing the vessel in question.

The present invention is also directed to a bistable valve. The valve, as shown generally at 600 in FIG. 19 includes a snap-action bipositional unit cell shown generally at 604 located within a conduit 606. Snap-action bipositional unit cell 604 consists of a (substantially arcuate) flexible member 608 having a first end 612 and a second end 616. First end 612 is in communication with a triggering means 620 which is supported, in turn by a support means 624 emerging from the inner surface of conduit 606. Second end 616 of flexible member 608 is anchored to stop surface 628 which extends across conduit 606. Support means 624 and stop surface 628 must be sufficiently rigid to hold flexible member 608 in place and must be more rigid than flexible member 608. Stop surface 628 extends substantially obliquely across conduit 606 in oblique regions 630 and has a opening 632 within in longitudinal region 634 to allow the flow therethrough of a fluid. Although opening 632 is oriented along the longitudinal axis 636 of conduit 606, those of ordinary skill in the art will recognize other possible orientations of the opening and stop surface. Valve closure member 640, actuated between open and closed positions by flexible member 608, is constructed and arranged so as to block the flow of fluid through opening 632 when flexible member 608 is in the closed position. When flexible member 608 is in the open position, as depicted in FIG. 20 valve closure member 640 no longer obstructs opening 632, thereby allowing the flow of fluid therethrough.

While triggering means 620 may be any suitable mechanical, hydraulic, pneumatic, or thermal based trigger known in the art at present or in the future, in a preferred embodiment, triggering means 620 is a piezoelectric element. In operation, if the piezoelement shown in FIG. 19 at 620 is not activated, valve closure member 640 is closed. Activation of piezoelement 620, as shown in FIG. 20 causes a small shortening in the longitudinal length (denoted by Y in FIG. 15) of piezoelement 620 which in turn releases flexible member 608 from its first position. With member 608 released, valve closure member 640 is free to open under the pressure transmitted from the fluid. Member 608 assumes a second, inverted, position, as depicted in FIG. 20 While the fluid pressure maintains member 608 in its second position, even in the absence of any fluid, member 608 remains in its second position, as depicted in FIG. 20 if the triggering is turned off and piezoelement 620 assumes its original length. Valve closure member 640 may be closed again, in the absence of fluid, by a subsequent triggering of piezoelement 620 allowing member 608 to transition to its second (closed) position which is the preferred position of member 608. Member 608 has been treated to receive a preferred position as shown in FIG. 3.

Figure 19:
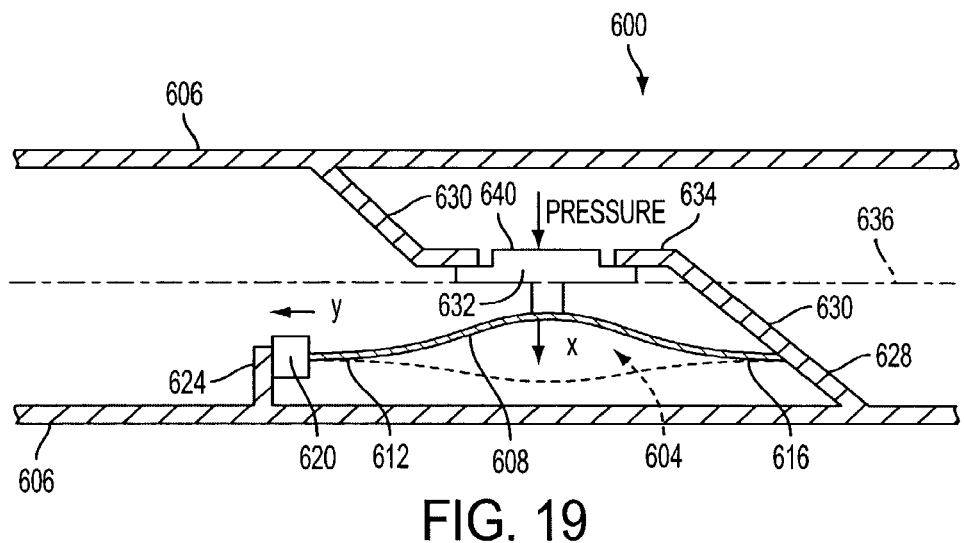
FIG. 19 shows a bistable valve in the closed position.
Figure 20:
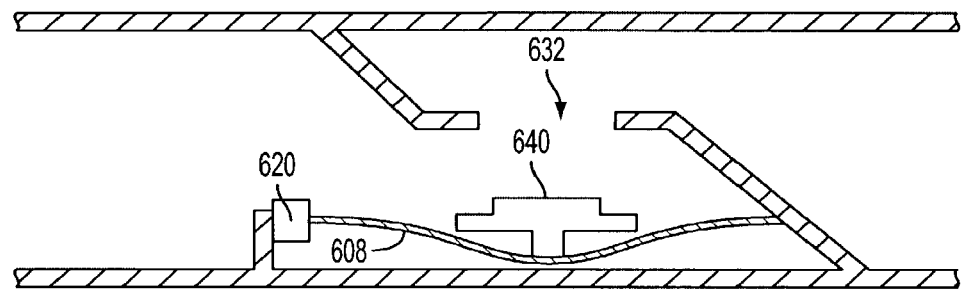
FIG. 20 shows the bistable valve of FIG. 19 in the open position.

The valve depicted in FIGS. 19 and 20 may be applied to medical and non-medical devices. It is, in particular, an aim of the present invention to apply the inventive bistable valve to the control of urinary incontinence. In a patient with incontinence, the above described valve may be implanted in the urethra using any suitable means including the use of the above-described expansion rings to clamp the valve to the urethra. Although the valve in the default state is closed, the valve may be triggered when the bladder is full, to void the bladder. Upon voiding the bladder, the valve may be triggered again to close it. Another such application is to employ the inventive valve in conjunction with a shunt. The shunt may be activated by triggering the device and similarly may be closed by triggering the device.

Of course the valve may be used in other medical and non-medical applications as well.

Figures 21A, 21B:
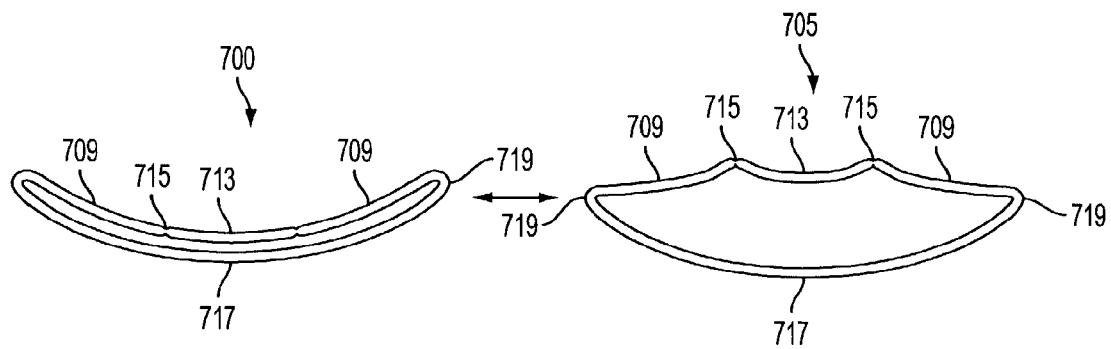
FIG. 21a shows a multistable cell in the fully contracted state.
FIG. 21b shows the multistable cell of FIG. 21a in the fully expanded state.

In addition to the bistable unit cells disclosed above, bistable unit cells and more generally, multistable unit cells of other shapes are also contemplated by the present invention. FIGS. 21*a* and 21*b* are schematic representations of another embodiment of an inventive hinged multistable cell in its contracted and expanded states, respectively. The contracted cell, shown generally at 700, and the expanded cell, shown generally at 705, consist of four interconnected relatively rigid members. Two side members 709 are connected to opposite ends of top member 713 via hinges 715. Side members 709 are connected at their opposite ends to opposite ends of bottom member 717 via hinges 719. Preferably, the hinges are elastic or plastically deformable. The hinges may be fixedly attached to the side, top and bottom members or may be integral with these members. In the latter case, the hinges may be formed by removing material from the cell in the region of the hinges so that the hinges are thinner or have a different geometry from the side, top and bottom members. In the process of transitioning from the expanded to the collapsed state, bottom member 717 opens slightly. The cell of FIGS. 21*a*,*b* also has two additional intermediate states in which one or the other (but not both) of side members 709 and top member 713 are collapsed downward.

Figures 22A, 22B:
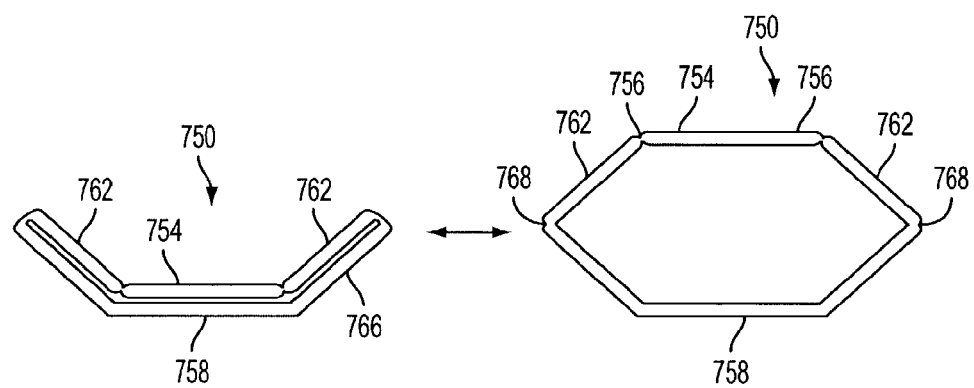
FIG. 22a shows another multistable cell in the fully contracted state.
FIG. 22b shows the multistable cell of FIG. 22a in the fully expanded state.

A hexagonal hinged multistable unit cell is shown schematically in FIG. 22*a* in the collapsed state and in FIG. 22*b* in the expanded state. The cell, shown generally at 750, consists of top member 754 and bottom member 758, and upper side members 762. Two upper side members 762 are connected to opposite ends of top member 754 via hinges 756. Upper side members 762 are connected to bottom member 758 via hinges 768. Bottom member 758 is shaped like a 'U' with the two uprights of the 'U' modified to lie at oblique angles with respect to the bottom part of the 'U'. As with the previously discussed inventive cells, hinges 756 and 768 may be elastic or plastically deformable and may be fixedly attached to the members or integral with the members. The hexagonal unit cell exhibits multiple stable states. In addition to the fully expanded and fully contracted states shown in FIGS. 22*a* and 22*b*, the hexagonal cell can also achieve two intermediate stable configurations in which only one of the two upper side members 762 is collapsed inward along with top member 754.

The above described hinged multistable cells may be used in any of the above discussed applications e.g. to form stents, clamps, clips, expander rings, bistable valves.

Figure 23:
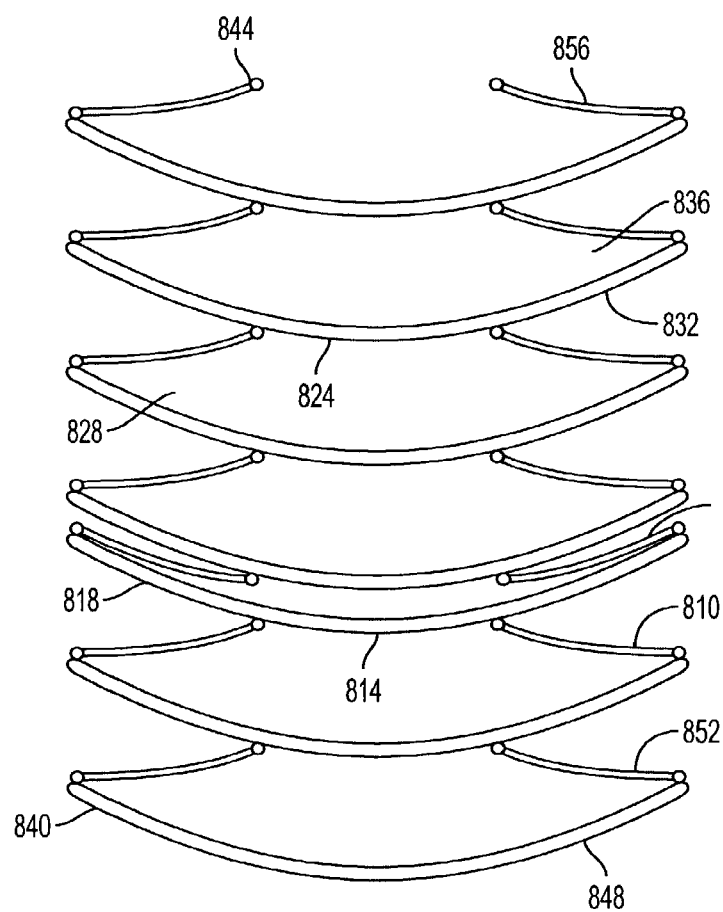
FIG. 23 shows several unit cells as shown in FIGS. 21a,b joined together and in the fully expanded state.

In one such application a ring or stent is formed of the hinged cells of FIGS. 21*a* and 21*b*. As shown in FIG. 23, a series of unit cells of the type depicted in FIG. 21 are joined together so that the top member of a cell forms a portion of the bottom member of an adjoining cell. As depicted, top member 814 of cell 810 forms a portion of bottom element 818 of cell 820. Similarly, top member 824 of cell 828 forms a portion of bottom element 832 of cell 836. Although the ring or stent in FIG. 23 has been cut for illustrative purposes, the two ends 840 and 844 are normally joined together with a portion of lower member 848 of cell 852 serving as an upper member for cell 856. The ring so formed has a range of stable stable states including a fully expanded state and a fully contracted state. Where the individual cells are made identically, only the fully expanded states may be accessed by the application of a uniform radially outward force to the stent in the fully contracted state. It may serve as a clamp or collar, an expansion ring or a stent. Larger stents may be formed by interconnecting a plurality of such rings.

Figure 24A:
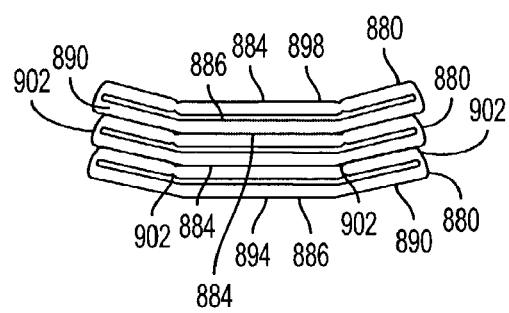
FIG. 24a shows several unit cells as shown in FIGS. 22a,b joined together and in the contracted state.
Figure 24B:
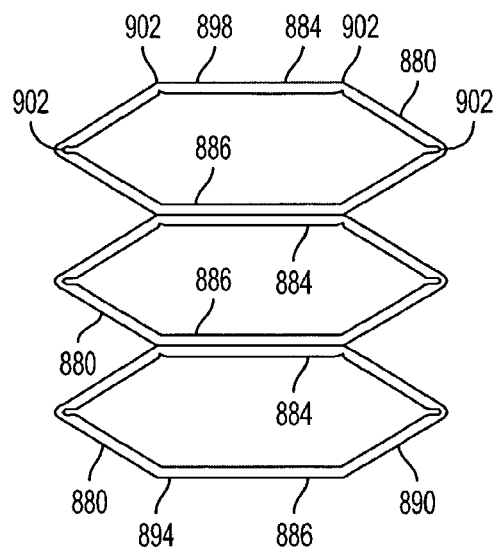
FIG. 24b shows the interconnected cells of FIG. 24a in fully expanded state.
Figure 24C:
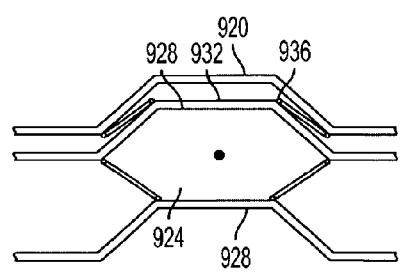
FIG. 24c shows the interconnected units cells of FIG. 24a in the process of expanding.
Figure 24D:
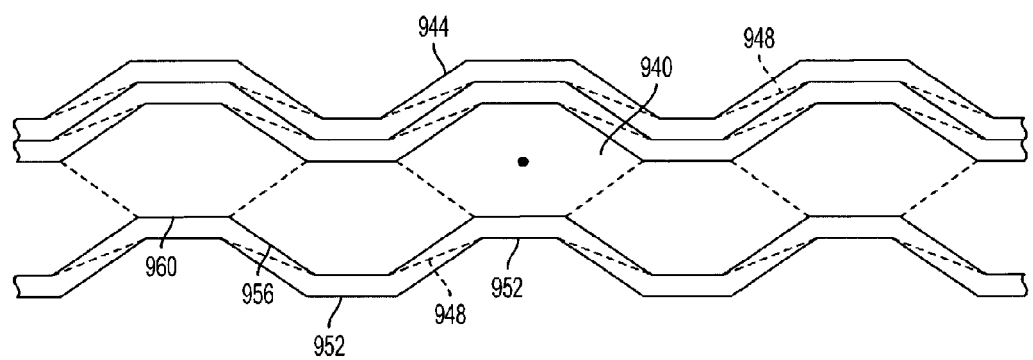
FIG. 24d shows several strips of interconnected cells as in FIGS. 24a,b joined together and in the process of expanding.

Similar products may also be formed from other multistable units cells. FIGS. 24*a* and 24*b* illustrate one such possibility schematically in which hexagonal unit cells such as those shown in FIGS. 22*a*,*b* may be joined together to form a ring. The top member 884 of each cell 880 is joined with a the bottom portion 886 or modified 'U' shaped bottom member 890. Although shown in strip form in FIGS. 24*a* and 24*b*, end 894 can be joined to end 898 to form a ring. The strip of FIG. 24*a* is shown in fully expanded state in FIG. 24*b*. Adjacent cells 880 are seen in their expanded state. For the sake of completeness, the hinges are designated 902. FIG. 24*c* shows one cell 920 in the process of expanding and one already expanded cell 924. The cells 920 and 924 are joined at bottom member 928 and top member 932. Hinges are shown at 936. Multiple strips may also be joined together so as to form a stent whose length is a multiple of the length of the unit cell. In such a case, upper side members of adjacent cells would be joined together. This is illustrated in FIG. 24*d* which, like FIG. 24*c* shows cells 940 in the expanded state and cells 944 in the process of expanding. Upper side members 948 are shown by dashed lines. Adjacent strips of interconnected cells 952 are joined together by upper side members 948 as well as by oblique regions 956 of bottom members 960.

It should be noted that the inventive devices of the present application may be use on a temporary basis or on a permanent basis in the body. Thus, for example, permanent stents and clamps are contemplated, as are removable stents and clamps.

It should further be noted that in expanding-some of the inventive multistable cells, there may be components of expansion/contraction in a direction perpendicular to the direction of the force applied to expand the cells.

Finally, for the purposes of this application, the term 'multistable' is intended to include 'bistable'.

In the described drawings and text only some examples of different embodiments have been given. While the stents of the present invention can appear similar to prior stents, the mechanical results are completely different due to the special combination of a rigid section and a more flexible section in the same unit cell. Of course there are, beside the illustrated sinusoidal shape many other possible basic shapes for the unit cells, with similar characteristic behavior.

From the above disclosure of the general principles of the present invention and the preceding detailed description, those skilled in this art will readily comprehend the various modifications to which the present invention is susceptible. It is intended for the coverage of the present application to include different geometries, different constructions and different combinations of one or more materials to obtain the same basic mechanical behavior as exhibited by the above described examples.

What is claimed is:

1. A medical device including at least one unit cell formed from at least two segments comprising a first relatively rigid arcuate segment; and a second relatively flexible arcuate segment, the first and second arcuate segments mechanically connected so that the first segment hinders the deformation of the second segment in a first direction, whereby the unit cell can be deformed in a second direction substantially perpendicular to the first direction, between a first substantially stable collapsed shape and a second substantially stable expanded shape,
   wherein a majority of the first relatively rigid arcuate segments are directly connected to the second relatively flexible arcuate segments of an adjacent unit cell by means of joints.

2. A medical device as in claim 1, the unit cell having an equilibrium position, the unit cell having a symmetrical load-displacement characteristic around the equilibrium position.

3. A medical device as in claim 1, the unit cell having an equilibrium position, the unit cell having an asymmetrical load-displacement characteristic around the equilibrium position, the most stable shape of the unit cell being the expanded shape.

4. A medical device as in claim 1, the unit cell having an equilibrium position, the unit cell having an asymmetrical load-displacement characteristic around the equilibrium position, the most stable shape of the unit cell being the collapsed shape.

5. A medical device as in claim 1 in the form of a clip for holding one or more body parts.

6. A medical device as in claim 1 in the form of an expander for holding one or more body parts apart.

7. A medical device as in claim 1 comprising a plurality of unit cells, each unit cell characterized by a point of maximum deflection of the second relatively flexible arcuate segment, wherein the joints are located at or near the point of maximum deflection of each of the second relatively flexible arcuate segments.

8. An expandable, hollow, stent, having the structure of claim 7, the stent having a plurality of stable configurations with different diameters, the stent having a fully collapsed configuration in which the stent has a minimum diameter and the stent having a fully expanded configuration in which the stent has a maximum diameter.

9. The stent of claim 8 made at least in part of a material selected from the group consisting of plastic deformable materials, elastically deformable materials, polymers, metals, composites, shape memory materials exhibiting superelastic behavior, shape memory materials exhibiting temperature sensitive behavior and combinations thereof.

10. A multiple unit stent comprised of a plurality of stents as in claim 8, the stents connected in the axial direction by flexible joints.

11. A stent as in claim 10 where the cells are balloon expandable, self-expanding or temperature sensitive.

12. A stent as claimed in claim 8 the stent being tubular and having one or more tapered cylindrical sections.

13. The medical device of claim 1 made at least in part of a material selected from the group consisting of plastic deformable materials, elastical deformable materials, polymers, metals, composites, shape memory materials exhibiting superelastic behavior, shape memory materials exhibiting temperature sensitive behavior and combinations thereof.

14. A stent as in claim 1 wherein the flexibility of the stent between adjacent unit cells in a tangential and/or axial direction is increased by disconnecting several unit cells from their adjacent unit cells by cutting a center of one or more joints.

15. A medical device including at least one unit cell formed from at least two segments comprising a first relatively rigid arcuate segment; and a second relatively flexible arcuate segment, the first and second arcuate segments mechanically connected so that the first segment hinders the deformation of the second segment in a first direction, whereby the unit cell can be deformed in a second direction substantially perpendicular to the first direction, between a first substantially stable collapsed shape and a second substantially stable expanded shape, wherein the first and second arcuate segments are connected by elastic hinges.

16. The medical device of claim 15, exhibiting increased flexibility wherein the first and second arcuate segments of the unit cells are connected by elastic hinges.

17. The medical device of claim 15, wherein the hinges are made of plastically deformable material.

18. A medical device as in claim 15, wherein adjacent unit cells in a tangential and/or axial direction are joined by plastic or elastic deformable hinges thereby increasing the flexibility between adjacent unit cells in a tangential and/or axial direction.

19. The medical device of claim 15, wherein the medical device exhibits increased flexibility via the elastic hinges.

20. A medical device including at least one unit cell formed from a first rigid arcuate segment and a second flexible arcuate segment, the first and second arcuate segments mechanically connected so that the first segment hinders the deformation of the second segment in a first direction, whereby the unit cell can be deformed in a second direction substantially perpendicular to the first direction, between a first substantially stable collapsed shape and a second substantially stable expanded shape,
   wherein a majority of the first rigid arcuate segments are directly connected to the second flexible arcuate segments of an adjacent unit cell by means of joints.

* * * * *